United States Patent [19]
Loy

[11] Patent Number: 5,979,446
[45] Date of Patent: Nov. 9, 1999

[54] REMOVABLE FALLOPIAN TUBE PLUG AND ASSOCIATED METHODS

[75] Inventor: Randall A. Loy, Longwood, Fla.

[73] Assignee: Synergyn Technologies, Inc., Longwood, Fla.

[21] Appl. No.: 09/177,307

[22] Filed: Oct. 22, 1998

[51] Int. Cl.⁶ .................................................... A61F 6/06
[52] U.S. Cl. ........................................... 128/830; 128/831
[58] Field of Search .................................... 128/830–841, 128/885; 600/29–31

[56] References Cited

U.S. PATENT DOCUMENTS

| | | |
|---|---|---|
| Re. 29,345 | 8/1977 | Erb . |
| 3,042,030 | 7/1962 | Read . |
| 3,397,699 | 8/1968 | Kohl .......................................... 128/349 |
| 3,648,683 | 3/1972 | Brodie . |
| 3,675,639 | 7/1972 | Cimber . |
| 3,687,129 | 8/1972 | Nuwayser . |
| 3,811,423 | 5/1974 | Dickinson ................................ 128/830 |
| 3,858,571 | 1/1975 | Rudolph . |
| 3,918,431 | 11/1975 | Sinnreich . |
| 3,990,434 | 11/1976 | Free . |
| 4,091,807 | 5/1978 | Dickinson ................................ 128/130 |
| 4,245,359 | 1/1981 | Stuhmer . |
| 4,302,855 | 12/1981 | Swanson . |
| 4,447,915 | 5/1984 | Weber . |
| 4,509,504 | 4/1985 | Brundin . |
| 4,512,342 | 4/1985 | Zaneveld et al. . |
| 4,523,590 | 6/1985 | Roth et al. . |
| 4,537,186 | 8/1985 | Verschoof et al. . |
| 4,579,110 | 4/1986 | Hamou . |
| 4,625,722 | 12/1986 | Murray . |
| 4,677,967 | 7/1987 | Zartman .................................... 128/830 |
| 4,682,592 | 7/1987 | Thorsgard . |
| 4,686,973 | 8/1987 | Frisch . |
| 4,805,618 | 2/1989 | Ueda et al. . |
| 4,815,454 | 3/1989 | Dozier, Jr. . |
| 5,065,751 | 11/1991 | Wolf . |
| 5,092,891 | 3/1992 | Kummer et al. . |
| 5,190,551 | 3/1993 | Chin et al. . |
| 5,222,964 | 6/1993 | Cooper . |
| 5,340,362 | 8/1994 | Carbone . |
| 5,431,660 | 7/1995 | Burke . |
| 5,474,089 | 12/1995 | Waynant . |
| 5,531,792 | 7/1996 | Huene . |
| 5,580,923 | 12/1996 | Yeung et al. . |
| 5,611,794 | 3/1997 | Sauer et al. . |
| 5,701,914 | 12/1997 | Loeffler . |

*Primary Examiner*—Michael A. Brown
*Attorney, Agent, or Firm*—Allen, Dyer, Doppelt, Milbrath & Gilchrist, P.A.

[57] ABSTRACT

A removable fallopian tube plug includes an elongated shaft member that has a diameter dimensioned for insertion into a human fallopian tube. The shaft has an imagable portion located at each of a distal end and a proximal end. A plurality of flexible fingerlike protrusions are affixed to at least a portion of the shaft, and are movable between a first position generally adjacent the shaft and a second position extending radially outward therefrom. The protrusions are biased to the second position and are adapted for closely engaging the fallopian tube when in the second position, and they are further arrayed radially and axially so as to form a barrier sufficient to prevent a passage of an ovum or a spermatozoa in an axial direction.

13 Claims, 7 Drawing Sheets

REMOVABLE FALLOPIAN TUBE PLUG AND ASSOCIATED METHODS

BACKGROUND OF THE INVENTION

1. Field of the Invention

The present invention relates to devices for blocking a bodily passage, and, more particularly, to such devices for removably blocking a fallopian tube.

2. Description of Related Art

Sterilization remains the most popular contraceptive method in the United States, particularly among women, with approximately 40% of all men and women combined relying on sterilization as a contraceptive method. Based upon 1988 date, approximately 600,000–700,000 female sterilizations are performed each year in the United States, with about 50% of these comprising postpartum tubal ligations via minilaparotomy.

Safe, nonpermanent physical methods of contraception are desirable for women who do not wish to or cannot take contraceptive medication. Since the intrauterine device (IUD) has been largely removed from the U.S. market, efforts have been expended to devise an effective fallopian tube plug to prevent the passage of an ovum into the uterus or of a spermatozoa toward an ovary.

Among the devices that have been disclosed are the fallopian tube plug of Heltebrandt et al. (U.K. Pat. Appl. GB 2 010 728 A), the plug and clip device of Roth et al. (U.S. Pat. No. 4,523,590), and the tubular pessary of Hamou (U.S. Pat. No. 4,579,110).

Over the past several years higher-quality flexible hysteroscopes having operating channels have become available, along with improved optics. It is believed that such devices can contribute to the development of an alternative reversible contraceptive method.

SUMMARY OF THE INVENTION

It is an object of the present invention to provide a device and method for blocking a fallopian tube.

It is an additional object to provide such a device that is removable.

It is a further object to provide such a device that is minimally invasive.

It is another object to provide such a device that is imagable to provide localization.

It is yet an additional object to provide such a device that does not cause scarification of the fallopian tube.

It is yet a further object to provide a reversible method for blocking a fallopian tube.

It is yet another object to provide such a method that can be performed on an out-patient basis with little or no anaesthesia.

An additional object is to provide a method of making a fallopian tube plug.

These objects and others are attained by the present invention, a removable fallopian tube plug that comprises an elongated shaft member that has a diameter dimensioned for insertion into a human fallopian tube. The shaft has an imagable portion located at least at each of a distal end and a proximal end.

A plurality of flexible fingerlike protrusions are affixed to at least a portion of the shaft, and are movable between a first position generally adjacent the shaft and a second position extending radially outward therefrom. The protrusions are biased to the second position and are adapted for closely engaging the fallopian tube. Further, the protrusions are arrayed radially and axially so as to form a barrier sufficient to prevent a passage of an ovum or of a spermatozoa in an axial direction.

It is preferred that the plug also comprise means for being gripped located at the proximal end in order to facilitate insertion and removal.

One of the methods of the present invention, for blocking a fallopian tube, includes grasping the plug as described above at a proximal end. The plug is then inserted through the cervix and into the ostium. The protrusions are dimensioned so as to be moved toward the first position during insertion into the tube, and then to be permitted to move toward the second position when insertion is complete, to closely engage the fallopian tube wall. Finally, the plug's proximal end is released, and the plug is permitted to remain within the tube until and if removal is desired.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

A description of the preferred embodiments of the present invention will now be presented with reference to FIGS. 1–6D.

Figure 1:
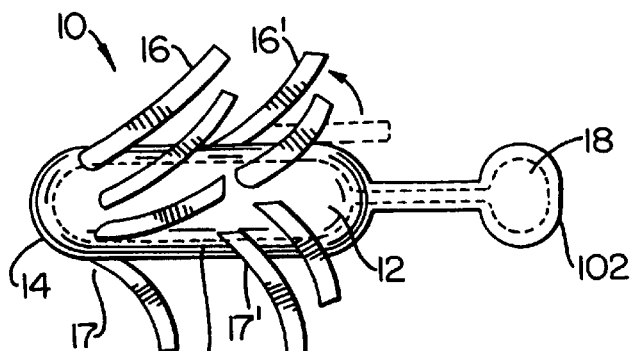
FIG. 1 is a side perspective view of a first embodiment of the fallopian tube plug of the present invention.
Figure 2:
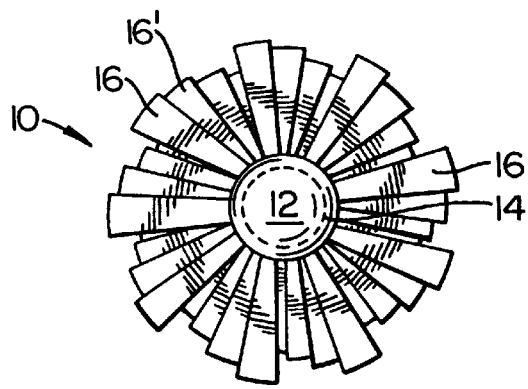
FIG. 2 is an end (axial) view of the first embodiment.
Figure 3:
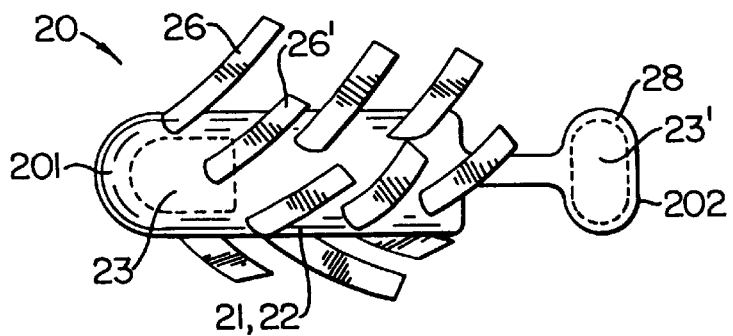
FIG. 3 is a side perspective view of a second embodiment of the fallopian tube plug of the present invention.

A first embodiment 10 of a fallopian tube plug is illustrated in FIGS. 1 and 2. The plug 10 comprises a shaft 11 that in turn comprises a relatively rigid rod 12 comprising a material that is imagable, such as, for example, by x-rays or ultrasound. This permits a noninvasive localization of the plug 10. An exemplary rod material comprises a metal such as stainless steel, although this is not intended as a limitation.

The shaft 11 further comprises a coating layer 14 that envelopes the core 12. The coating layer 14 comprises a biocompatible material such as a polymeric material. Exemplary polymeric materials comprise polytetrafluoroethylene and nylon, although these are not intended as limitations. In an alternate embodiment, the coating layer 14 comprises a compressible material with memory, such as a foamlike material.

The plug 10 additionally comprises a plurality of finger-like protrusions 16 that are coformed with the coating layer 14. The preferred polymeric material is believed to be beneficial owing to its inert and atraumatic characteristics. Their being integrally formed with the coating layer 14 significantly lessens the chance of breaking off and remaining in the tube after removal of the plug 10.

The protrusions 16 are formed along at least a portion of the shaft 11, and are movable between a first position generally adjacent the shaft 11 and a second position extending radially outward from the shaft 11. The protrusions 16 are biased to the second position and are adapted for closely engaging the fallopian tube.

The protrusions 16 are arrayed radially and axially so as to form a barrier sufficient to prevent a passage of an ovum or a spermatozoa in an axial direction (see FIG. 2). In this embodiment the protrusions 16 are arrayed in a plurality of axially spaced-apart rows 17, such that each protrusion 16 in a row 17 is radially offset from an adjacent protrusion 16' in an adjacent row 17'. Thus in viewing the plug 10 along an axial direction the protrusions 16 would be seen to present a fully occluded appearance, which would serve to prevent the passage of an ovum or a spermatozoa thereby.

The plug 10 also comprises a grip knob 18 at the proximal end 102 that facilitates insertion and removal of the plug 10. Typically in use the plug 10 is inserted and removed with the use of an insertion device, such as, but not intended to be limited to, a flexible-tip-type hysterofiberscope 30 (see FIGS. 5A–5D). This instrument has a pair of movable jaws 31 that can grip and lock on the knob 18 during the insertion and removal processes. Alternatively, or a forceps F may be used, as in FIGS. 6A–6D.

In a second embodiment (FIGS. 3 and 4), a fallopian tube plug 20 comprises a shaft 21 that in turn comprises a relatively rigid rod 22 comprising a biocompatible material such as a polymeric material. As above, exemplary polymeric materials comprise polytetrafluoroethylene and nylon, although these are not intended as limitations.

The shaft 21 further comprises a pair of locators 23, 23' that are embedded in the rod 22 adjacent the distal 201 and proximal 202 ends, respectively. The locator material should be imagable, such as, for example, by x-rays, ultrasound, or hysterosalpingogram, again permitting a noninvasive localization of the plug 20. An exemplary locator material comprises a metal such as stainless steel, although this is not intended as a limitation.

The plug 20 additionally comprises a plurality of finger-like protrusions 26 that are coformed with the rod 22. Again, a polymeric material such as polytetrafluoroethylene or nylon is believed to be beneficial owing to its inert and atraumatic characteristics. Their being integrally formed with the rod 22 significantly lessens the chance of breaking off and remaining in the tube after removal of the plug 20.

As with the first embodiment, the protrusions 26 are formed along at least a portion of the shaft 21, and are movable between a first position generally adjacent the shaft 21 and a second position extending radially outward from the shaft 21. The protrusions 26 are biased to the second position and are adapted for closely engaging the fallopian tube.

Figure 4:
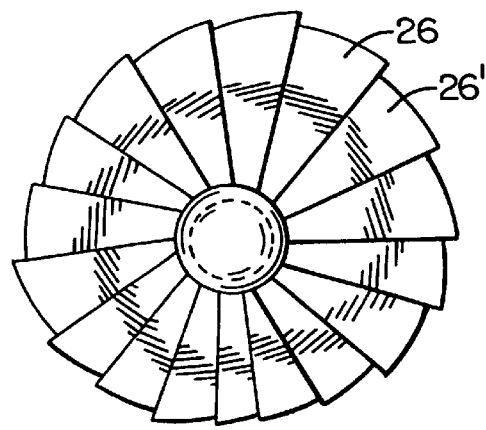
FIG. 4 is an end (axial) view of the second embodiment.

The protrusions 26 are arrayed radially and axially so as to form a barrier sufficient to prevent a passage of an ovum or a spermatozoa in an axial direction (see FIG. 4). In this embodiment the protrusions 26 are arrayed in generally helical fashion, so that each protrusion 26 is radially and axially offset from an adjacent protrusion 26'. Thus in viewing the plug 20 along an axial direction the protrusions 26 would be seen to present a fully occluded appearance, which would serve to prevent the passage of an ovum or a spermatozoa thereby.

The plug 20 also comprises a grip knob 28 at the proximal end 202 that facilitates insertion and removal of the plug 20.

One preferred embodiment of a method of inserting either of the plugs 10,20 as described above (FIGS. 5A–5D) comprises the steps of creating an access into the uterus U and fallopian tube FT such as by means well known in the art, typically including inserting a speculum into the vagina V and sterilizing with a solution such as Betadine. In some patients one or both of the steps of effecting a paracervical block, such as by using a 1% lidocaine solution with epinephrine, and performing a dilatation of the cervix C may be necessary or desired.

A flexible hysteroscope H, preferably of the type including visualization means such as fiber optic illumination and viewing elements, is employed as an insertion device. Such a device that fulfills these requirements includes, but is not intended to be limited to, a hysterofiberscope "HYF$_{TYPE}$1T" (Olympus, Lake Success, N.Y.), having an outside diameter appropriate for such an application, such as 4.9 mm.

The hysteroscope H is inserted through the cervical os COS using a physiologic saline solution such as intravenous fluid as a uterine distension medium. A blood pressure cuff pressurized, for example, at 150 mmHg or a 30–60 cc syringe may be employed to increase in-line pressure.

Figure 5A:
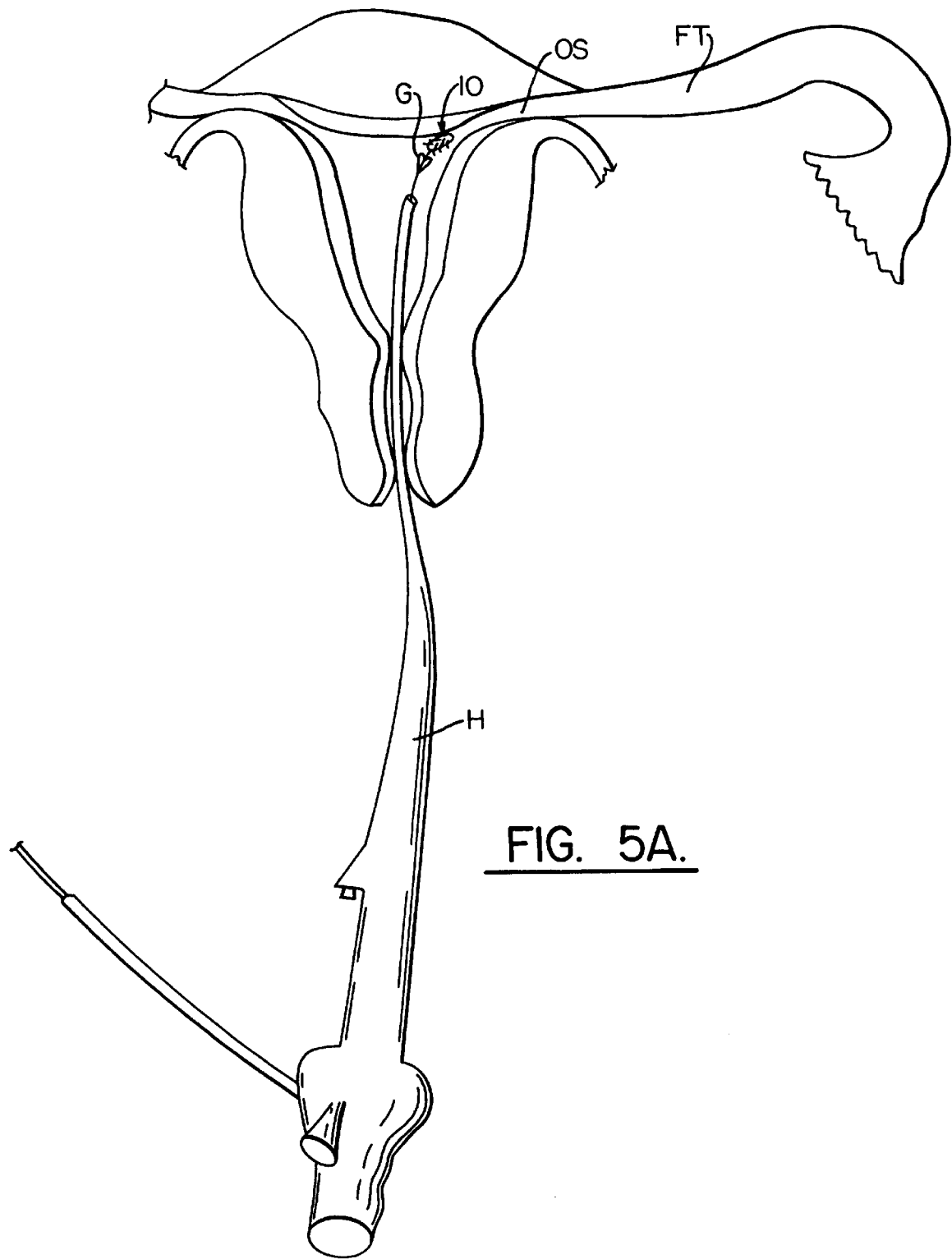
FIG. 5 illustrates a first method of inserting the fallopian tube plug, including: (A) grasping the plug with an insertion device; (B) passing the plug and distal end of the insertion device into the ostium; (C) releasing the plug from the insertion device; and (D) withdrawing the insertion device, leaving the plug within the fallopian tube.
Figure 5B:
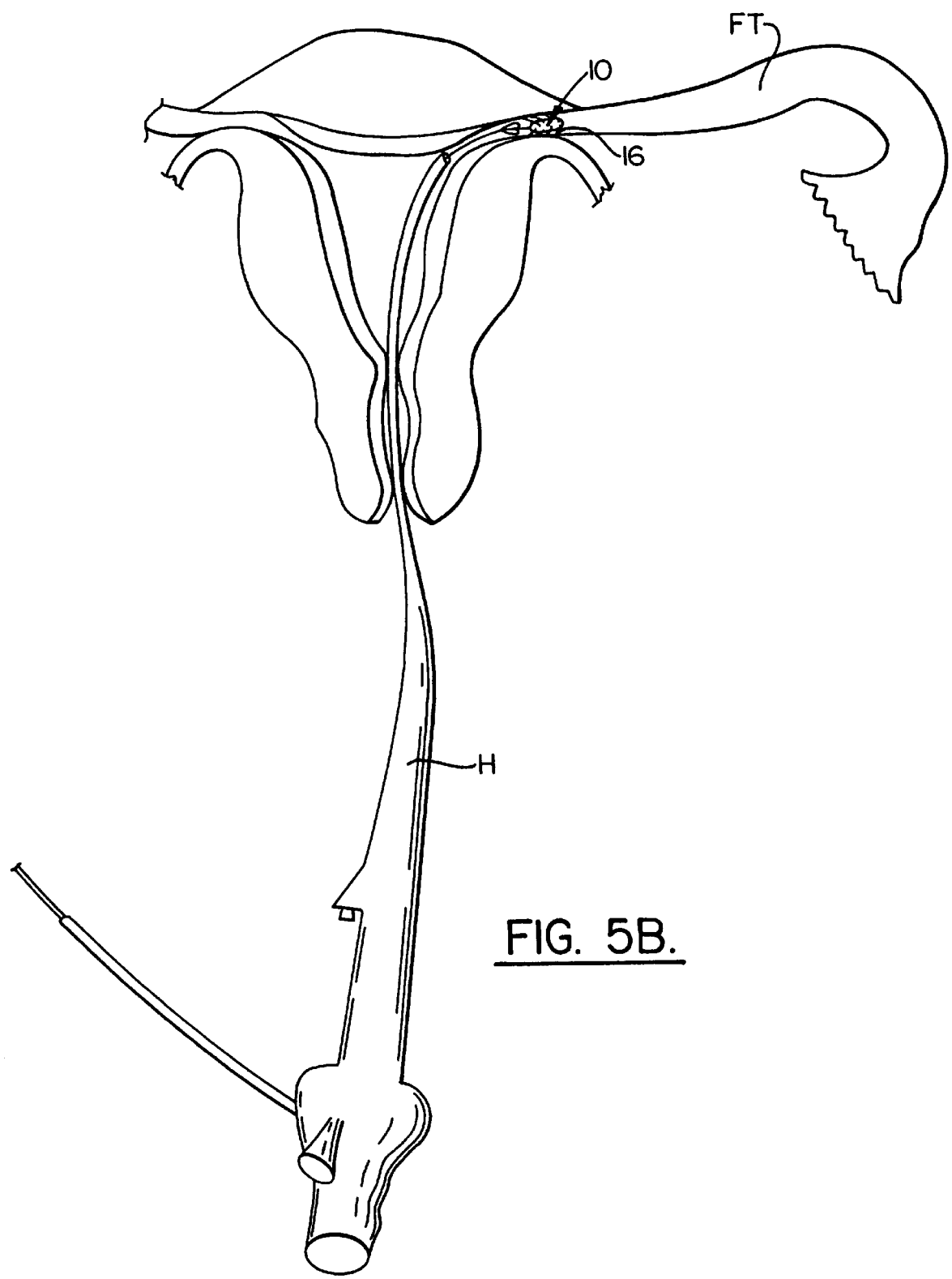
Figure 5C:
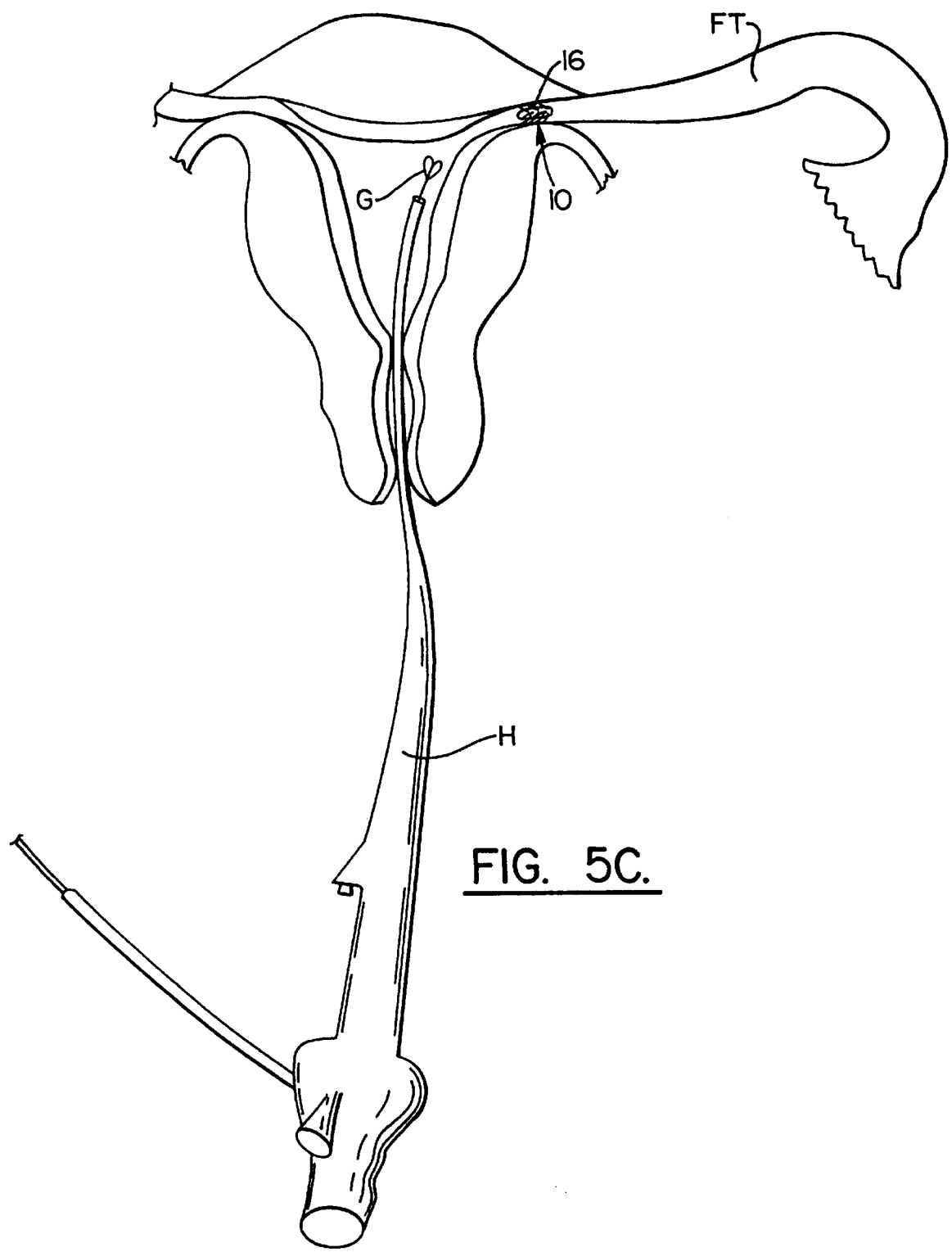
Figure 5D:
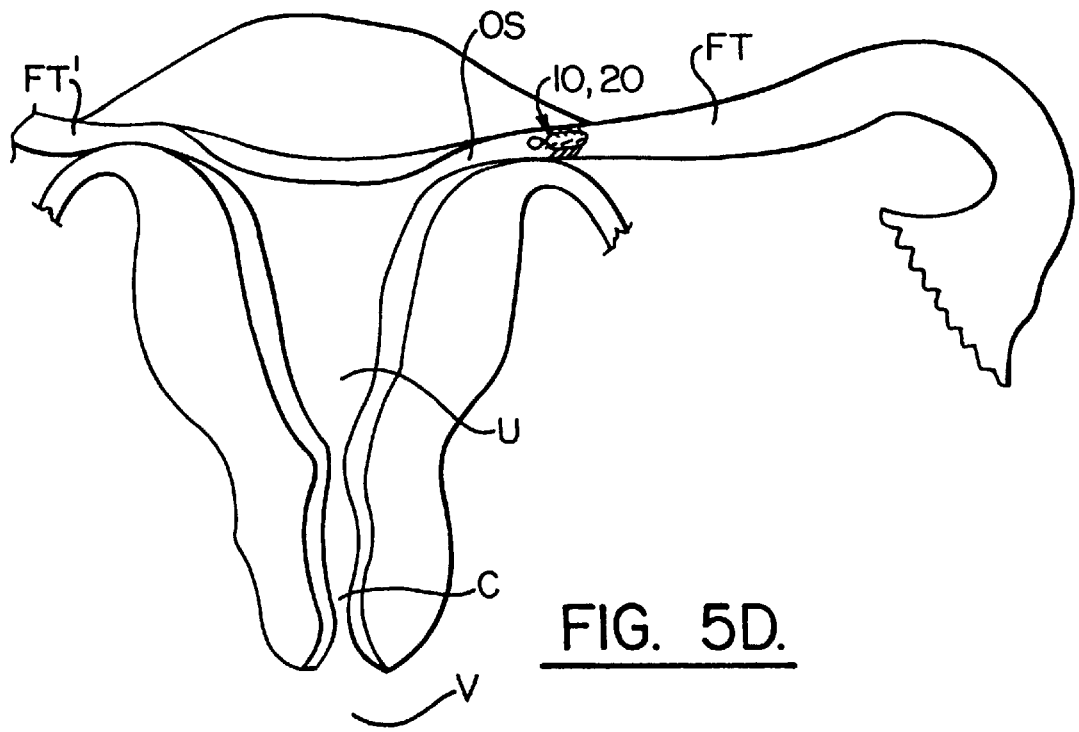

A forceps-type grasper G inserted through the distal end of the scope H is used to grasp the plug 10 or 20 at the proximal end 102,202 (FIG. 5A). The plug 10 or 20 is then inserted into the ostium OS to a desired location within the tube FT (FIG. 5B). The plug 10 or 20 is then pulled proximally slightly in order to fully deploy the protrusions 16,26 toward the second position to closely engage the fallopian tube wall. Next the plug's proximal end 102,202 is released from the forceps (FIG. 5C), and the scope H is removed, leaving the plug 10,20 in place (FIG. 5D).

Typically the plug insertion steps are repeated to insert a second plug 10,20 into the contralateral side's fallopian tube FT'.

Preferably a test should be performed to ensure that occlusion of the tube has been achieved. Such a test may include, for example, attempting to pass air bubbles in a solution past the plugs.

The plug(s) 10,20 can be localized after insertion by imaging, such as by x-radiography or ultrasound, owing to the presence of the imagable portions at the proximal 102,202 and distal 101,201 ends.

Figure 6A:
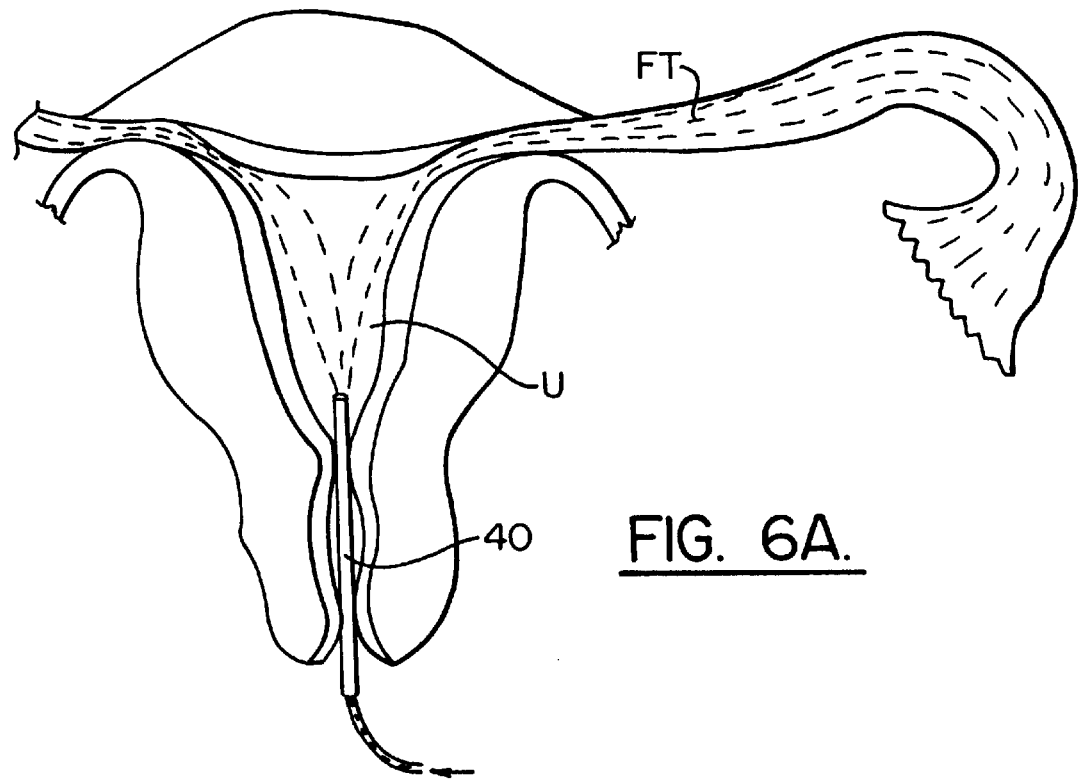
FIG. 6 illustrates a second method of inserting the fallopian tube plug, including (A) obtaining a hysterosalpingogram; (B) inserting a second catheter and injecting contrast material; (C) removing second catheter and inserting a plug; and (D) injecting additional contrast medium to determine tubal occlusion.

A second method of performing fallopian tube FT occlusion comprises the steps of creating an access into the uterus U as above, and determining a patent fluid pathway such as, for example, by hysterosalpingography, wherein radio-opaque fluid material is injected through a first catheter 40 into the uterus U and a visualization of the area provides an indication as to the patency or occlusion of the fallopian tubes FT and to determine the position of the cornu CO (FIG. 6A).

Figure 6B:
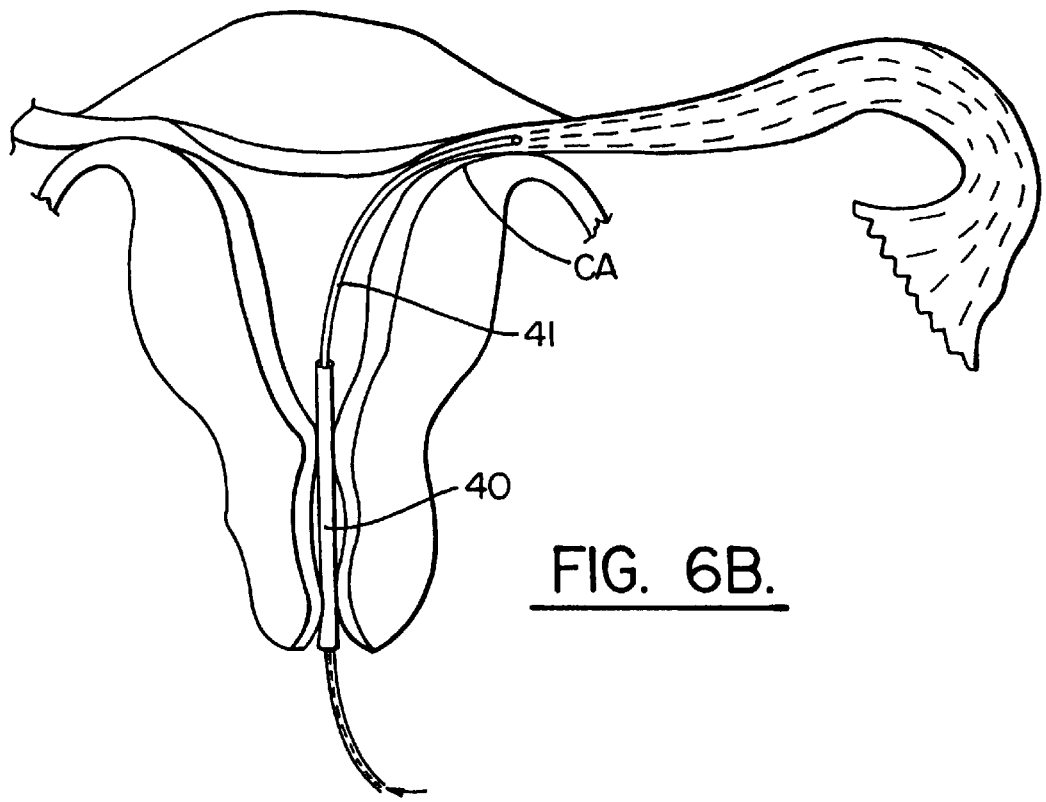

A second cathether 41, which is narrower than the first catheter 40, and further is curved, is inserted through the first catheter 40 and wedged into the cornual angle CA. Further contrast material is inserted through the second catheter 41 to determine the patency of this region (FIG. 6B). Exemplary catheters 40,41 usable in this procedure may comprise, but are not intended to be limited to, coaxial catheters 9 F and 5.5 F, respectively.

Figure 6C:
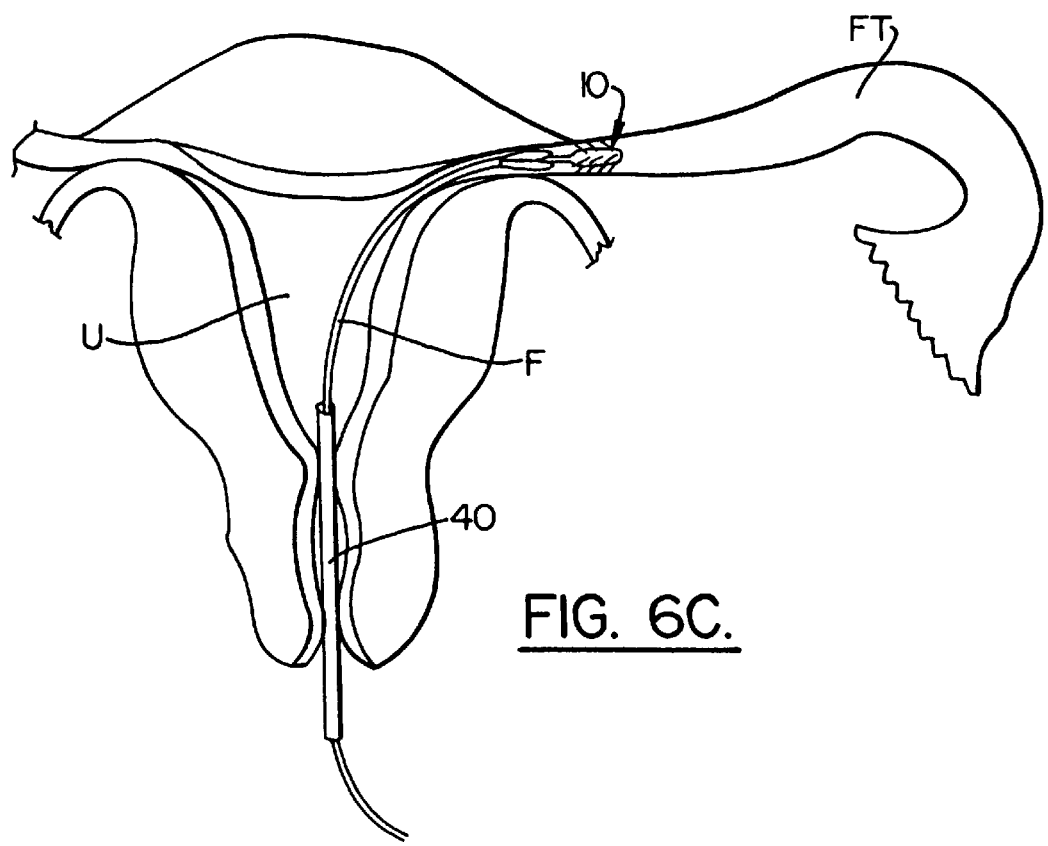

The second catheter 41 is removed, and the distal end of a grasping forceps F, having been used to grasp the tube plug's knob 18, is placed through the first catheter 40, to position a plug 10 (FIG. 6C). The forceps F are removed, and the procedure of FIGS. 6B and 6C are repeated if desired contralaterally.

Figure 6D:
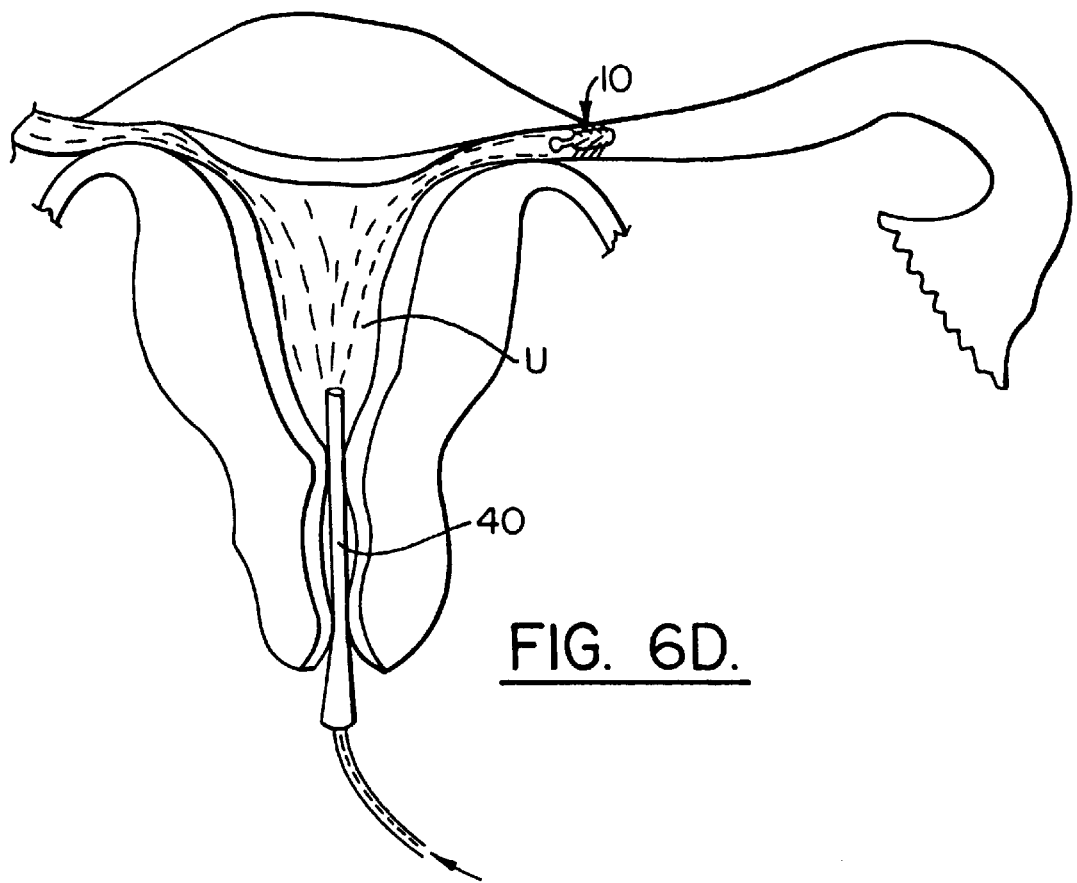

Additional contrast medium is injected to determine if the tubal occlusion were successful (FIG. 6D). If not, the procedure is repeated, with the tubal plug 10 being wedged more tightly until full occlusion is achieved.

The tubal occlusion methods of the present invention are believed to represent procedures easily performed in an office setting, on an outpatient basis, without general anaesthesia. It is believed that a relatively small dose of a relaxant (such as Valium) and/or anti-inflammatory (such as a nonsteroidal anti-inflammatory drug) is sufficient medication under which to perform the procedures.

It may be appreciated by one skilled in the art that additional embodiments may be contemplated, including alternate materials and alternate arrangements of the occluding protrusions.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A removable fallopian tube plug comprising:
   an elongated shaft member having a diameter dimensioned for insertion into a human fallopian tube, the shaft comprising a core comprising a rigid, imagable rod and a coating layer enveloping the core comprising a polymeric material; and
   a plurality of flexible finger protrusions affixed to at least a portion of the shaft, the protrusions movable between a first position generally adjacent the shaft and a second position extending radially outward therefrom, the protrusions biased to the second position and adapted for closely engaging the fallopian tube, the protrusions further arrayed radially and axially so as to form a barrier sufficient to prevent a passage of an ovum or a spermatozoa in an axial direction.

2. The fallopian tube plug recited in claim 1, wherein the protrusions and the coating layer are co-formed from the polymeric material.

3. The fallopian tube plug recited in claim 1, wherein the polymeric material is selected from a group consisting of polytetrafluoroethylene, nylon, and a compressible foam.

4. The fallopian tube plug recited in claim 1, wherein the rod comprises a metal.

5. The fallopian tube plug recited in claim 4, wherein the metal comprises stainless steel.

6. A removable fallopian tube plug comprising:
   an elongated shaft member having a diameter dimensioned for insertion into a human fallopian tube, the shaft comprising a generally rigid rod having an imagable material affixed at a distal end and at a proximal end; and
   a plurality of flexible finger protrusions affixed to at least a portion of the shaft, the protrusions movable between a first position generally adjacent the shaft and a second position extending radially outward therefrom, the protrusions biased to the second position and adapted for closely engaging the fallopian tube, the protrusions further arrayed radially and axially so as to form a barrier sufficient to prevent a passage of an ovum or a spermatozoa in an axial direction.

7. The fallopian tube plug recited in claim 6, wherein the rod comprises a polymeric material and the imagable material comprises a metal embedded in the rod adjacent the distal end and adjacent the proximal end.

8. The fallopian tube plug recited in claim 7, wherein the protrusions and the rod are co-formed from the polymeric material.

9. A method for blocking a fallopian tube comprising the steps of:
   grasping a fallopian tube plug at a proximal end, the plug comprising:
     an elongated shaft member having a diameter dimensioned for insertion into a human fallopian tube, the shaft having an imagable portion located at each of a distal end and the proximal end; and
     a plurality of flexible finger protrusions affixed to at least a portion of the shaft, the protrusions movable between a first position generally adjacent the shaft and a second position extending radially outward therefrom, the protrusions biased to the second position and adapted for closely engaging the fallopian tube, the protrusions further arrayed radially and axially so as to form a barrier sufficient to prevent a passage of an ovum or a spermatozoa in an axial direction;
   inserting the plug through the cervix and into the ostium, the protrusions moving toward the second position to closely engage the fallopian tube wall;
   releasing the plug proximal end; and
   permitting the plug to remain within the fallopian tube.

10. A method for blocking a fallopian tube comprising the steps of:
   determining a patency of a fallopian tube;
   wedging a catheter into a cornual angle of the fallopian tube;
   determining a patency of the fallopian tube with the catheter wedged therein;
   removing the catheter;
   grasping a fallopian tube plug at a proximal end, the plug comprising:
     an elongated shaft member having a diameter dimensioned for insertion into a human fallopian tube, the shaft having an imagable portion located at each of a distal end and the proximal end; and
     a plurality of flexible finger protrusions affixed to at least a portion of the shaft, the protrusions movable between a first position generally adjacent the shaft and a second position extending radially outward therefrom, the protrusions biased to the second position and adapted for closely engaging the fallopian tube, the protrusions further arrayed radially and axially so as to form a barrier sufficient to prevent a passage of an ovum or a spermatozoa in an axial direction;

inserting the plug through the cervix and into the ostium, the protrusions moving toward the second position to closely engage the fallopian tube wall;

releasing the plug proximal end; and permitting the plug to remain within the fallopian tube.

11. The method recited in claim 10, wherein the patency determining steps each comprise performing a hysterosalpingogram.

12. The method recited in claim 10, further comprising the step, following the step of permitting the plug to remain within the fallopian tube, of redetermining fallopian tube patency.

13. The method recited in claim 10, further comprising repeating the steps thereof for a contralateral fallopian tube.

* * * * *